United States Patent [19]

Welford et al.

[11] Patent Number: 4,529,305

[45] Date of Patent: Jul. 16, 1985

[54] EXAMINING A GEMSTONE

[76] Inventors: Walter T. Welford, 8, Chiswick Rd., London; Andrew D. G. Stewart, The Old Rectory, Ashampstead, Reading, Berkshire; John S. Dodson, 20, Leigh Rd., Cobham, Surrey, all of England

[21] Appl. No.: 395,245

[22] Filed: Jul. 6, 1982

[30] Foreign Application Priority Data

Aug. 3, 1981 [GB] United Kingdom ............... 8123661

[51] Int. Cl.³ .......................................... G01N 21/87
[52] U.S. Cl. ..................................... 356/30; 356/376
[58] Field of Search ................... 356/30, 376; 358/96

[56] References Cited

U.S. PATENT DOCUMENTS 3,244,065  4/1966  Lemelson ............................. 354/78
3,625,618  12/1971  Bickel ................................ 356/376

OTHER PUBLICATIONS

Herron, R. E., "The Light Beam Profiler—Past, Present, and Future", SPIE, vol. 283, 3-D Machine Perception, (1981), pp. 61-65.

Primary Examiner—F. L. Evans
Attorney, Agent, or Firm—Shapiro and Shapiro

[57] ABSTRACT

Method and apparatus for examining a gemstone to determine a parameter thereof. A thin beam of light is projected onto the stone, the beam is moved relative to the stone, the position where the beam strikes the stone is sensed in a direction different from that in which the beam is projected, and a parameter is determined making use of information derived from such sensing.

21 Claims, 6 Drawing Figures

EXAMINING A GEMSTONE

BACKGROUND OF THE INVENTION

It is desirable to be able to determine at least one parameter of a gemstone automatically or semi-automatically. While a principal purpose of the present invention is to predict the largest polished stone or the most profitable polished stores, that can be obtained from a stone, be it rough, sawn, cleaved, part manufactured (e.g. bruted or blocked) or polished and in need of repair (the word "parameter" as used herein includes such a prediction), the invention, as noted in GB No. 2 081 439 A, is more broadly applicable for determining parameters such as the following (which are exemplary only and not limitative):

in the case of cut (i.e. polished) stones, the make in general (the make is the shape and size of the stone, including the angles and sizes of the parts of the stone as a whole and of the facets);

the profile, in general terms;

the maximum and minimum girdle diameters;

the average or mean girdle diameter;

the table diameter as a percentage of the average or mean girdle diameter;

the crown height as a percentage of the average or mean girdle diameter;

the girdle width (the dimension measured normal to the table);

the pavilion depth;

the pavilion angle;

the angles or lengths of the secondary facets;

the volume;

in the case of bruting, re-measure the bruted stone e.g. to brute further or to determine the correct angle for polishing;

in the case of a rough stone or a sawn half, the largest possible bruted or polished, i.e. brilliant cut, stone of given proportions which can be fitted inside (this can be associated with centering for subsequent bruting or coning, and more details are given in GB No. 2 080 712A)—this can also take account of grain and of unwanted areas such as pique (an inclusion within a stone);

suitable proportions or angles for polished stone;

suitable "swindling", specially if reentrants or other defects are present—"swindling" is a term covering e.g. having the culet off centre, having girdle out of round or tilting the girdle; in the case of a cut stone (particularly a fancy stone, i.e. a stone of irregular shape), the size and shape of the recess in the setting for receiving the stone.

THE INVENTION

The invention provides a method of examining a gemstone, comprising:

projecting a thin beam of light onto the stone;

causing relative motion between the beam and the stone;

sensing the position where the beam strikes the stone, as viewed in a direction different from that in which the beam is projected; and determining a parameter of the stone making use of information derived from sensing said position.

The invention also provides apparatus for examining a gemstone, comprising:

means for supporting the gemstone;

means for rotating the stone supporting means about an axis of rotation;

means for projecting a thin beam of light onto the stone, whereby the stone moves relative to the beam, the beam being a thin band in cross-section, with its long dimension being parallel to the stone's axis of rotation and great enough to strike the entire axial length of the stone;

means for sensing the position where the beam strikes the stone, as viewed in a direction making a small angle to that in which the beam is projected; and means for determining a parameter of the stone making use of information derived from sensing said position.

When the position where the beam strikes the stone is viewed in a direction different from that in which the beam is projected, the illuminated zone of the stone will not be straight and will give an indication of the profile of the stone where the beam strikes the stone.

The invention is particularly useful where there are shallow reentrants in the stone. Provided the angle between the axis of projection and the axis of viewing is small, relatively shallow reentrants can be examined.

In general, the greater the angle between the axis of projection and the axis of viewing, up to 90°, the greater the accuracy (the more the profile is exaggerated), but also the greater the danger of not determining the bottom of a reentrant. The preferred value for said angle is about 30°.

Accuracy can be improved if two, spaced, parallel thin beams are projected onto the stone, the respective said positions being sensed. Another alternative is to project a single beam of light but to view in two different directions, on either side of the beam.

DESCRIPTION OF PREFERRED EMBODIMENTS

The invention will be further described, by way of example, with reference to the accompanying drawings, in which.

Figure 1:
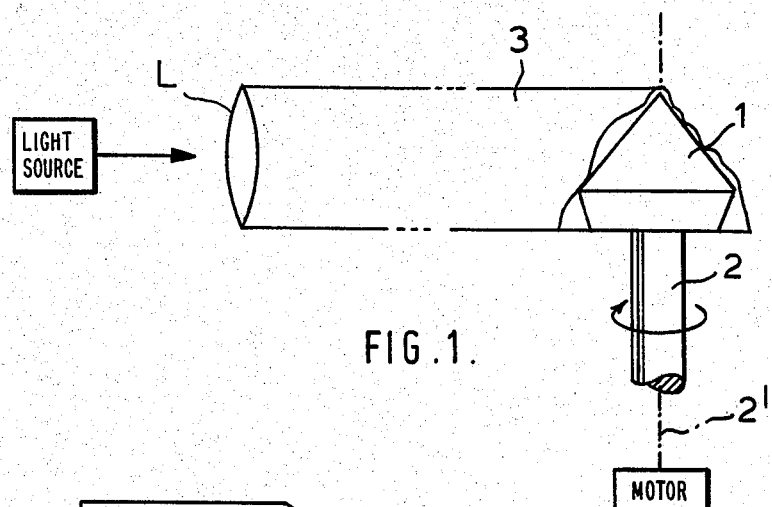
FIG. 1 is a schematic elevation of apparatus in accordance with the invention.

In FIG. 1, a sawn but otherwise uncut diamond 1 is shown in profile, supported by the end of a rotary spindle 2 (rotating about its axis 2') which is driven by a motor (so designated). If desired, the spindle 2 can be hollow and the arrangement can be such that the diamond 1 is held on the end of the spindle 2 by light suction. The motor can be a stepping motor or alternatively a continuous drive motor, for instance strobing the light source (discussed later). In the case of a stepping motor, as is described in GB No. 2 081 439 A, referred to above, the speed can, for example, be up to 1,000 steps per second (say 400 steps per second), the rotational movement occupying only a small fraction of the total time.

Figure 2:
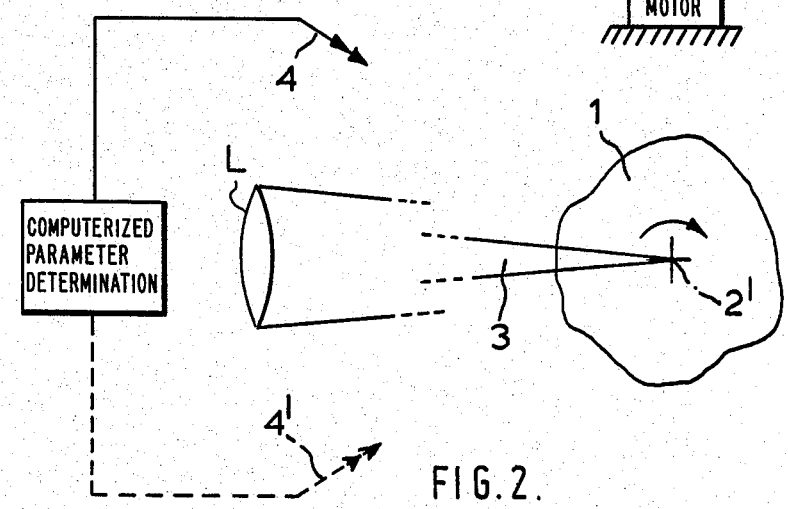
FIG. 2 is a schematic plan of the embodiment of FIG. 1.

A stationary, thin beam 3 of light is projected onto the diamond 1—the thin beam can be referred to as a sliver or thin slice. The thin beam 3 can be obtained in a conventional manner such as by a suitable light source (so designated) in combination with a convex lens L, such techniques being well known in the art. As can be seen in FIG. 1, the thin beam 3 is projected onto the diamond 1 at right angles to the direction of rotation, and the beam 3 is a thin band in vertical cross-section, the long dimension being vertical, i.e. parallel to the axis of rotation of the diamond 1 and intersecting said axis (or rather being such that it would intersect said axis if the diamond 1 were not present); the long dimension is great enough to strike the whole axial length of the diamond 1 (through not the whole width). As shown in FIG. 2, the thin beam 3 is focussed on the axis of rotation 2' of the diamond 1; however, this is not obligatory—for instance, the focus may be roughly half way between the axis and the maximum diameter of the diamond 1, i.e. slightly shorter than that shown in FIG. 2.

In order to sense the position where the thin beam 3 strikes the diamond 1 as viewed in a direction different from that in which the thin beam 3 is projected, there is a T.V. viewer, indicated by the double-headed arrow 4 in FIG. 2. Throughout this specification the T.V. viewer or viewers are only indicated schematically as their provision would present no problems to a skilled man. For instance, as stated in GB No. 2 081 439 A, the viewer 4 may be a two-dimensioned charge couple device, producing a purely electronic signal. The axis of viewing makes a small angle (shown as about 30° in FIG. 2 but it could be say 20°) to the axis of projection. Also, it will be observed that the viewing axis and the axis of projection of the beam lie on different radials of the axis of rotation 2.

Figure 3:
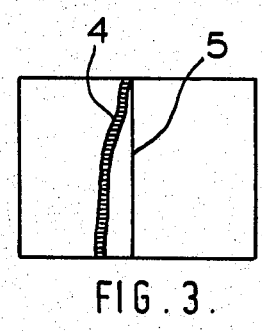
FIG. 3 shows the thin beam or slice, as viewed on the stone.

FIG. 3 is a representation of the illuminated zone on the diamond 1 as it would be seen on a T.V. screen, though it will be appreciated that no screen is necessary. The distance of the image 4 from the centre line 5 represents the distance of the surface of the diamond 1 from the axis of the spindle 2, and more particularly the image 4 gives the x and y coordinates of any point on the surface of the diamond 1 illuminated by the thin beam 3 at that instant. Using this information, any appropriate parameter can be determined automatically with a suitable computing facility, such a facility being diagrammatically illustrated in FIG. 2. More particularly, as discussed in previously referred to GB No. 2 081 439 A, for example, viewer 4 may be connected through a suitable electronic unit to an associated computer (direct memory access transfer) and the aforementioned T.V. screen. The computer may of course be linked to a machine tool if, for example, a blank is being cut or a mold formed preparatory to setting a fancy stone, or the computer may produce a magnetic or punched card for controlling such a tool.

Figure 4:
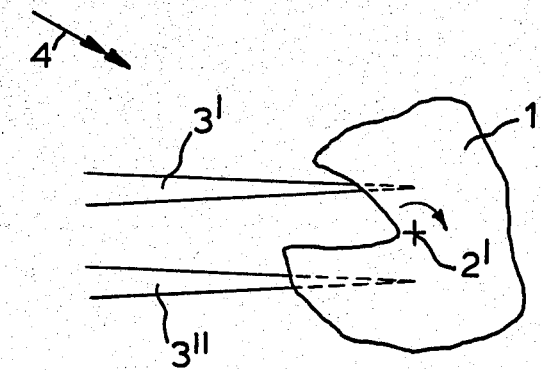
FIGS. 4, 5 and 6 are schematic plans of further apparatus in accordance with the invention.

As indicated in FIG. 4, two, spaced, thin beams 3', 3" can be projected onto the diamond 1, the illuminated zones being sensed by a single viewer 4. The interpretation of the images is easier if the beams 3', 3" are parallel. As shown in FIG. 4, neither beam 3', 3" intersects the axis of the spindle 2, but if desired, one of the beams could intersect such axis.

As indicated in dashed lines in FIG. 2, a second T.V. viewer 4' (which would also be connected to the computing facility, as indicated in the drawing) can be used, so as to view the illuminated zone on the diamond 1 in two different directions, both different from that in which the beam 3 is projected, preferably with the axis of the thin beam 3 bisecting the axes of the viewers 4, 4'.

Figure 5:
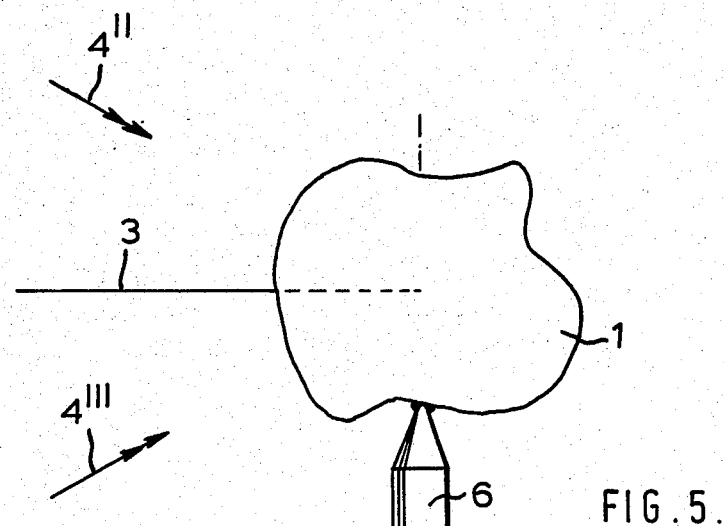

As indicated in FIG. 5, the diamond 1 can be cemented to the tip of a thin support such as a pin 6 which is rotated about an axis 6'. The diamond 1 is illuminated with a thin beam 3 (only the axis is shown but its long cross-sectional dimension is parallel to the sheet, i.e. the beam 3 is in the plane of the drawing, the plane containing the axis 6' of rotation of the pin 6). Two T.V. viewers 4" and 4"' are represented as being one above and one below the thin beam 3, enabling the "poles" of the diamond 1 to be viewed, but the viewers 4" and 4"' must be out of the plane of the drawing, i.e. not in the same vertical plane as the thin beam 3; in practice, the arrangement can be as indicated in the preceding paragraph, in which case there would be one thin beam and four viewers, or as indicated in FIG. 4, in which case there would be two thin beams and two viewers.

Figure 6:
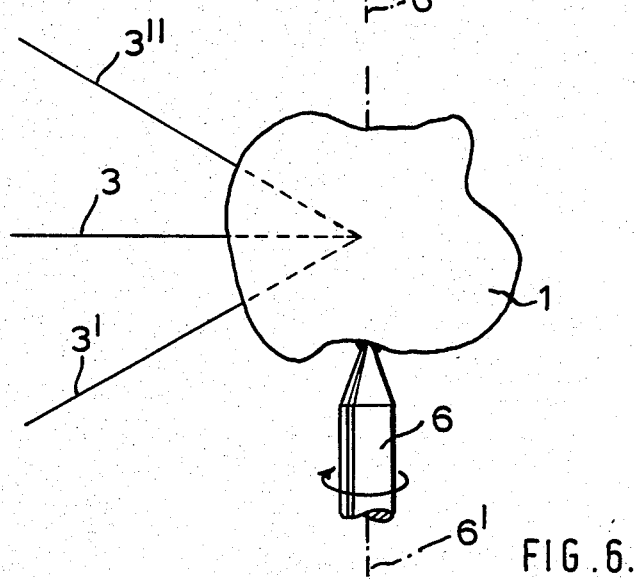

In FIG. 6, 3, 3' and 3" indicate the axes of three thin beams in the plane of the drawing, the pin 6 being rotated about its axis 6'. The beams 3, 3", 3"' in effect illuminate a thin strip from pole to pole of the diamond 1. Any suitable viewing mode can be used, e.g. one viewer on the equator (as in FIGS. 1 and 2), two viewers on the equator (see viewers 4, 4' in FIG. 2), or four viewers, two above the equator and two below the equator.

We claim:

1. A method of examining a gemstone, comprising:
   projecting a thin beam of light onto the stone;
   causing relative movement between the beam and the stone about an axis of rotation;
   sensing the position where the beam strikes the stone, as viewed in a direction making a small angle to that in which the beam is projected so that the viewing direction and the direction in which the beam is projected intersect the surface of the stone at different locations;
   and determining a parameter of the stone making use of information derived from sensing said position.

2. The method of claim 1, in which the stone is rotated relative to the beam.

3. The method of claim 2, in which the beam is projected onto the stone generally at right angles to the direction of relative rotation.

4. The method of claim 1, wherein said sensing includes viewing said position with a T.V. viewer.

5. The method of claim 4, wherein said determining includes calculating said parameter with a computer facility connected to said T.V. viewer.

6. The method of claim 3, wherein said angle is about 20 degrees or about 30 degrees.

7. A method of examining a gemstone, comprising projecting a thin beam of light onto the stone; rotating the stone relative to the beam; sensing the position where the beam strikes the stone, as viewed in a direction making a small angle to that in which the beam is projected; and determining a parameter of the stone making use of information derived from sensing said position and wherein the beam is projected onto the stone generally at right angles to the direction of relative rotation and further wherein the beam is a thin band in cross-section, the long dimension being parallel with the axis of relative rotation of the stone, and the long dimension of the beam being great enough to strike the whole axial length of the stone.

8. A method of examining a gemstone, comprising projecting a plurality of thin beams of light onto the stone and rotating the stone relative to the beams, the beams respectively having a long dimension gret enough to strike the whole axial length of the stone and being projected at least from either side of the equator but lying substantially in a plane containing the axis of relative rotation of the stone so that a thin band with long dimension parallel to the axis of relative rotation is projected onto substantially the whole axial length of the stone, the method further including sensing the positions where the beams strike the stone, as viewed in a direction different from that of each beam, and determining a parameter of the stone making use of information derived from sensing said positions.

9. The method of claim 7, wherein said positions are sensed as viewed in at least two different directions, both different from the directions in which the beams are projected.

10. A method of examining a gemstone comprising projecting two spaced, parallel thin beams of light onto the stone; causing relative movement between the beams and the stone; sensing the respective positions where the beams strike the stone, as viewed in a direction different from that in which the beams are projected; and determining a parameter of the stone making use of information derived from sensing said positions.

11. A method of examining a gemstone, comprising projecting a thin beam of light onto the stone; causing relative movement between the beam and the stone; sensing the position where the beam strikes the stone, as viewed in at least two directions both different from that in which the beam is projected; and determining a parameter of the stone making use of information derived from sensing said position.

12. Apparatus for examining a gemstone, comprising:
means for supporting the gemstone;
means for rotating said stone supporting means about an axis of rotation;
means for projecting a thin beam of light onto the stone, whereby the stone moves relative to the beam, said beam being a thin band in cross-section, with its long dimension being parallel to the axis of rotation of the stone and great enough to strike the entire axial length of the stone;
means for sensing the position where the beam strikes the stone, as viewed in a direction making a small angle with that in which the beam is projected; and
means for determining a parameter of the stone making use of information derived from sensing said position.

13. The apparatus of claim 12, wherein said viewing direction and the direction in which said beam is projected lie along different radials of said axis of rotation.

14. The apparatus of claim 12, including two of said sensing means located for sensing said position as viewed in two different directions.

15. The apparatus of claim 12, wherein said sensing means comprises a T.V. viewer.

16. The apparatus of claim 12, wherein said angle is of about 20 degrees or about 30 degrees.

17. A method of examining a gemstone, comprising projecting a thin beam of light onto the stone; causing relative movement between the beam and the stone; sensing the position where the beam strikes the stone, as viewed in a direction different from that in which the beam is projected; and determining, making use of information derived from sensing said position, the polished stone or stones that can be obtained by working the stone under examination.

18. A method of examining a gemstone, comprising rotating the stone about an axis of rotation; projecting a thin beam of light onto the stone whereby the stone moves relative to the beam, the beam being a thin band in cross-section, with its long dimension being parallel to the axis of rotation and great enough to strike the whole axial length of the stone; sensing the position where the beam strikes the stone, as viewed in a direction different from that in which the beam is projected; and determining a parameter of the stone making use of information derived from sensing said position.

19. The method of claim 18, wherein said viewing direction lies along a radial of said axis of rotation and wherein said projecting is in a direction lying along a different radial of said axis of rotation.

20. The method of claim 18, wherein said sensing includes sensing the position where the beam strikes the stone, as viewed in at least two different directions, both different from and making a small angle to that in which the beam is projected.

21. The method of claim 18, wherein said direction makes an angle of about 20 degrees or about 30 degrees to the direction in which the beam is projected.

* * * * *